| United States Patent [19]
Moore

[11] Patent Number: 4,916,226
[45] Date of Patent: Apr. 10, 1990

[54] OPTICAL RESOLUTION METHOD FOR 3S-(3-PYRIDYLMETHYL)-6-(2-QUINOLYL)-METHOXY-4S-CHROMANOL

[75] Inventor: Bernard S. Moore, Waterford, Conn.

[73] Assignee: Pfizer Inc., New York, N.Y.

[21] Appl. No.: 389,714

[22] Filed: Aug. 4, 1989

[51] Int. Cl.$^4$ .................................... C07D 405/14
[52] U.S. Cl. .................................................. 546/176
[58] Field of Search ...................................... 546/176

[56] References Cited
PUBLICATIONS

H. Gilman (Ed). Organic Chemistry, vol. I, 2nd Ed., Wiley (1943), N.Y., N.Y., pp. 232, 233 and 254–259.

*Primary Examiner*—David B. Springer
*Attorney, Agent, or Firm*—Peter C. Richardson; J. Trevor Lumb; Robert K. Blackwood

[57] ABSTRACT

Preparative method for 3S-(3-pyridylmethyl)-6-(2-quinolyl)methoxy-4S-chromanol via its salt with natural tartaric acid.

3 Claims, No Drawings

OPTICAL RESOLUTION METHOD FOR 3S-(3-PYRIDYLMETHYL)-6-(2-QUINOLYL)-METHOXY-4S-CHROMANOL

BACKGROUND OF THE INVENTION

The present invention is directed to a process for 3S-(3-pyridylmethyl)-6-(2-quinolyl)methoxy-4S-chromanol, of the formula

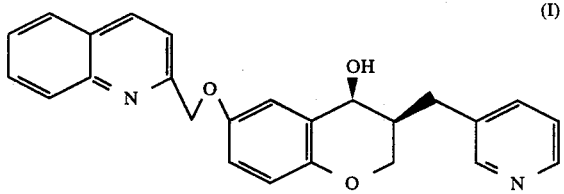

alternatively named 3S,4S-[(3-pyridyl)methyl]-6-[(2-quinolyl)methoxy]-3,4-dihydro-2H-benzopyran-4-ol. In this process, the corresponding racemic compound, (±)-cis-(3-pyridylmethyl)-6-(2-quinolyl)methoxy-4-chromanol is resolved using tartaric acid (also known as natural tartaric acid or L-tartaric acid), with isolation of the pure, crystalline, less-soluble, tartrate salt of (I) from ethyl acetate.

The compound (I) is a known inhibitor of 5-lipoxgenase enzyme and antagonist of leukotriene receptors, and is thus useful in the prevention or treatment of asthma, arthritis, psoriasis, ulcers, myocardial infarction and related disease states in mammals, as detailed in published European patent application No. 313295.

The compound (I) was heretofore obtained by resolution of (±)-cis-(3-pyridylmethyl)-6-(2-quinolyl)methoxy-4-chromanol by means of chromatographic separation of derived (R)-(−)-O-acetylmandelate esters. This method involves the discrete chemical steps of esterification and hydrolysis, and in addition, a tedious chromatographic separation step. Thus it has been a desirable goal to find a method for the direct resolution of the corresponding racemate in the form of a preferentially crystallized diastereomeric salt with an optically-active acid, a goal which has been met by the present invention.

Natural L-tartaric acid has been previously used in the resolution of racemic organic amines. However, its use does not assure success in any given instance, since it requires not only that the desired diastereomeric salt, be crystalline, but that it be significantly less soluble than its structurally, very closely related diastereomeric salt, if the desired salt is to be obtained in good yield without tedious fractional crystallization methods. See Wheland, "Advanced Organic Chemistry," 3rd Ed., John Wiley and Sons, Inc., New York, 1960, page 312; and "Left and Right Drugs," Science 84, American Association for the Advancement of Science, Washington, D.C., June, 1984, page 11.

A hydrated L-tartrate salt was previously prepared from acetone by combining already resolved compound of the formula (I) with L-tartaric acid in acetone; EP No. 313295 cited above.

SUMMARY OF THE INVENTION

The present invention is directed to a method for the preparation of optically active 3S-(3-pyridylmethyl)-6-(2-quinolyl)methoxy-4S-chromanol, of the absolute stereochemical formula (I) depicted above, or a pharmaceutically acceptable salt thereof, which comprises the steps of:

(a) combining racemic cis-3-(3-pyridylmethyl)-6-(2-quinolyl)methoxy-4-chromanol with at least a half molar quantity of L-tartaric acid in ethyl acetate at a temperature in the range of about 20°–65° C., at a concentration such that the L-tartrate salt of the compound of the formula (I) crystallizes substantially free of the L-tartrate salt of the enantiomer of (I);

(b) conventionally recovering said L-tartrate salt of the compound of the formula (I); and (c) conventionally treating said L-tartrate salt with base in a reaction-inert solvent to produce said compound of the formula (I).

As used above and elsewhere herein, the expression "reaction-inert solvent" refers to a solvent (or solvent mixture) which does not interact with starting materials, reagents, intermediates or products in a manner which adversely affects the yield of the desired product.

The present invention is also directed to the above process which further comprises recovering from step (a) mother liquors of the crude L-tartrate salt of enantiomeric 3R-(3-pyridylmethyl)-6-(2-quinolyl)methoxy-4R-chromanol, hydrolyzing the salt to the free base, oxidizing the alcohol group to form the corresponding 3R-ketone, racemizing same to form racemic 3-(3-pyridylmethyl)-6-(2-quinolyl)methoxy-4-chromanone, an intermediate readily reconverted to the starting material of above step (a).

DETAILED DESCRIPTION OF THE INVENTION

The present invention is readily carried out. Thus, racemic cis-3-(3-pyridylmethyl)-6-(2-quinolyl)methoxy-4-chromanol is simply combined in ethyl acetate with at least 0.5 molar equivalents of L-tartaric acid (also known as natural tartaric acid or ordinary tartaric acid), usually about 1 molar equivalent of tartaric acid to facilitate recovery of the diastereomeric salt, i.e., the undesired enantiomer, for recycling. The amount of ethyl acetate is set at a level which leads to minimal or no concurrent recovery of the undesired salt (about 90–150 ml of ethyl acetate/g of racemate when the desired salt is isolated at ambient temperature, i.e., in the range of about 20°–28° C.). In any event, any co-recovered enantiomer is readily removed by repulping in fresh ethyl acetate, in which, because of its very low solubility, losses of the desired product are minimal. The reaction is facilitated by using thoroughly milled L-tartaric acid to facilitate its dissolution, and prolonged digestion of the reaction mixture, e.g., for 18 or more hours at ambient temperature or for generally lesser periods of time at elevated temperatures ranging up to the reflux temperature of the mixture, but preferably at more moderate temperatures, e.g., 40°–50° C. It is preferred to isolate the desired product after further digestion at ambient temperature.

The intermediate L-tartrate salt is conventionally hydrolyzed to form the desired enantiomeric free base of the above formula (I) with a strong base (at least one molar equivalent) in a reaction-inert solvent. Particularly convenient is an alkali metal hydroxide (such as NaOH) in water in the presence of a water immiscible organic solvent such as methylene chloride which will extract the desired free base as it is formed. Temperature is not critical, but is conveniently ambient so as to avoid the cost of heating or cooling. The product is conventionally recovered from the organic solvent, e.g., by stripping and/or by addition of a non-solvent.

For purposes of recycling, the crude 3R,4R-enantiomer, preferably in the form of its diastereomeric L-tartrate salt, is conventionally recovered from mother liquors by stripping and/or addition of a non-solvent. This salt is hydrolyzed as above, oxidized [for example, with Jones Reagent, according to methods detailed in EP No. 313295 (cited above and exemplified below)], and the resulting ketone racemized by the action of a strong base in a reaction-inert solvent (e.g., with about 10 mol % of sodium methoxide in methanol) at a temperature generally in the range of 0°–50° C., conveniently at ambient temperature. For purposes of recycling, the racemic ketone is converted to the corresponding racemic 4-chromanol, which is the starting material of the present invention, according to the method of Examples 4A and 230 of said EP patent reference. The same starting material is otherwise prepared according to Preparations 1–3 and Examples 1, 2, 3, 4, 4A, 5, 5A, 55, 228, 229 and 230 of that same reference.

The present invention is illustrated by the following examples, but is not limited to the details thereof.

EXAMPLE 1

3S-(3-Pyridylmethyl)-6-(2-quinolyl)methoxy-4S-chromanol (I)

A reaction flask equipped with stirrer and thermometer was charged with 5.0 liters ethyl acetate, milled L-tartaric acid (15.1 g, 0.10 mol) and (+)-cis-3-(pyridylmethyl)-6-(2-quinolyl)methoxy-4-chromanol (39.9 g, 0.10 mol). The stirred slurry was warmed to 40° C. for 2 hours, then to 50° C. for 2 hours and finally cooled slowly to 25° C. The L-tartrate salt of present title product (25.4 g after vacuum drying at 40° C. for 3 hours) was recovered by filtration. The filtrate was stripped to 200 ml and the crude, diastereomeric salt (27.1 g, suitable for recycling as noted below) recovered by filtration. Crude title product was purified by repulping in 1.5 liters of ethyl acetate; stirred for 4 hours at 50° C. and slowly cooled to 25° C. to recover 21.3 g of the purified L-tartrate salt of present title product; m.p. 143°–150° C. (cloudy); [alpha]$_D^{25}$ = −59.5° (c=0.6, CH$_3$OH). Stripping the repulp liquor produced an additional 3.1 g of crude diastereomeric salt suitable for recycling.

The purified L-tartrate of title product (21.0 g, 0.038 mol) was added in portions to a mixture of aqueous NaOH (4.0 g, 0.1 mol in 200 ml of H$_2$O) and CH$_2$Cl$_2$ (200 ml). The mixture was stirred 0.5 hour, the organic layer separated and the aqueous layer washed 2×75 ml fresh CH$_2$Cl$_2$. The organic layers were combined, backwashed 3×100 ml H$_2$O, treated with 2 g of activated carbon, dried (Na$_2$SO$_4$), stripped to 20 ml, twice diluted with 50 ml acetone and restripped to 25 ml, cooled to 15° C. and stirred for 0.5 hour, and present title product (11.8 g vacuum dried at 40° C. for 2 hours) recovered by filtration; m.p. 139°–141° C.; [alpha$_D^{20}$ = −98.6° (CH$_3$OH, c=0.74).

MS (m/e) 398 (M+ 100%), 288, 263, 256, 238 and 142. IR (CHCl$_3$) 3589, 3244, (OH), 1618, 1600 and 1577 cm$^{-1}$.

$^1$H—NMR(CDCl$_3$)delta(ppm): 2.24 (m, C—3H), 2.16 (dd, J=14, 8 Hz, 1CH$_2$Ar), 2.89 (dd, J=14, 8 Hz, 1CH$_2$Ar), 4.02 (m, OCH$_2$), 4.41 (d, J=3 Hz, C—4H), 5.22 (s, CH$_2$O), 6.75 (d, J=8 Hz, C—8H), 6.83 (d, J=2 Hz, C—5H), 6.86 (dd, J=8, 2 Hz, C—7H), 7.2 (m, 1ArH), 7.49 (m, 1ArH), 7.57 (m, 2ArH), 6.67 (ddd, J=8, 8, 2 Hz, 1ArH), 7.77 (d, J=8 Hz, 1ArH), 7.98 (d, J=8 Hz, 1ArH), 8.11 (d, J=8 Hz, 1ArH), 8.42 (m, 1ArH) and 8.49 (d, J=2 Hz, 1ArH).

Analysis calculated for C$_{25}$H$_{22}$N$_2$O$_3$: C, 75.36; H, 5.56; N, 7.03%. Found: C, 75.06; H, 5.36; N, 7.00%.

EXAMPLE 2

Recycled cis-3-(3-Pyridylmethyl)-6-(2-quinolyl)methoxy-4-chromanone

To a 5° C. mixture of 22.2 g (55.7 mmol) of crude 3R,4R-by-product of Example 1 in 75 ml of water is added 5.9 ml (111 mmol) of concentrated sulfuric acid. To this solution is added 300 ml acetone, and then 79.6 ml (55.7 mmol) of 0.7M Jones Reagent is rapidly added. The resultant mixture is stirred 1 hour at 25° C. and then added to saturated sodium bicarbonate (300 ml). The quenched reaction mixture is extracted twice with 150 ml ethyl acetate and once with 150 ml dichloromethane. The combined organic extract is dried over magnesium sulfate and evaporated to yield crude 3R-ketone. The latter is heated to reflux in methanol in the presence of 0.1 molar equivalent of sodium methoxide for 16 hours to effect racemization. Crude title product is isolated by neutralization with acetic acid, evaporated and purified by column chromatography on silica gel eluted with 92:3:3–90:5:5 dichloromethane:isopropanol:ethyl acetate and recrystallized from ethyl acetate-hexane to give present title product identical with that of Example 229 of EP 313295. This ketone is reduced to the alcoholic starting material of Example 1 by the method of Examples 4A and 230 of that same reference.

I claim:

1. A method for the preparation of 3S-(3-pyridylmethyl)-6-(2-quinolyl)methoxy-4S-chromanol of the formula

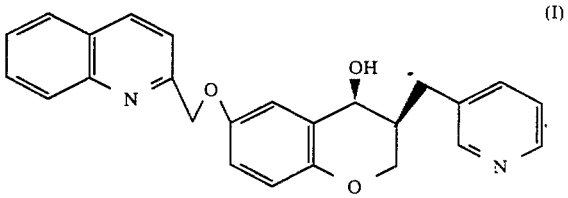

or a pharmaceutically acceptable salt thereof, which comprises the steps of:

(a) combining racemic cis-3-(3-pyridylmethyl)-6-(2-quinolyl)methoxy-4-chromanol with at least a half-molar quantity of L-tartaric acid in ethyl acetate at a temperature in the range of about 20° C. to about 65° C., at a concentration such that the L-tartrate salt of the compound of the formula (I) crystallizes substantially uncontaminated by the L-tartrate salt of the enantiomer of the compound of the formula (I);

(b) conventionally recovering said L-tartrate salt of the compound of the formula (I); and (c) conventionally treating said L-tartrate salt with base in a reaction-inert solvent to produce said compound of the formula (I).

2. A process of claim 1 wherein the molar quantity of L-tartaric acid is in the range of about 0.5 to 1.5.

3. A process of claim 1 which further comprises recovering as by-product crude L-tartrate salt of enantiomeric 3R-(3-pyridylmethyl)-6-(2-quinolyl)methoxy-4R-chromanol from the mother liquors of said L-tartrate salt of the compound of the formula (I), basic hydrolysis of said 3R,4R-salt to form corresponding 3R,4R-free base, oxidation of said free base with Jones Reagent to form the corresponding 3R,4-chromanone, and racemization of said 3R,4-chromanone to form racemic 3-(3-pyridylmethyl)-6-(2-quinolyl)methoxy-4-chromanone.

* * * * *